United States Patent [19]

Sherwin

[11] Patent Number: 4,709,702
[45] Date of Patent: Dec. 1, 1987

[54] ELECTROENCEPHALOGRAPHIC CAP

[75] Inventor: Gary W. Sherwin, South Huntingdon Township, Westmoreland County, Pa.

[73] Assignee: Westinghouse Electric Corp., Pittsburgh, Pa.

[21] Appl. No.: 727,031

[22] Filed: Apr. 25, 1985

[51] Int. Cl.⁴ ............................................. A61B 5/04
[52] U.S. Cl. .................................. 128/644; 128/731; 128/791
[58] Field of Search .............. 128/639, 644, 731, 791, 128/783, 640, 643

[56] References Cited

U.S. PATENT DOCUMENTS

| | | | |
|---|---|---|---|
| 2,409,033 | 11/1941 | Garceau | 128/644 |
| 2,549,836 | 6/1946 | McIntyre et al. | 128/644 |
| 3,505,993 | 12/1965 | Lewes et al. | 128/643 |
| 3,508,541 | 4/1970 | Westbrook et al. | 128/644 |
| 3,692,925 | 9/1972 | Kinkij | 174/36 |
| 3,735,753 | 5/1973 | Pisarski | 128/644 |
| 3,776,228 | 12/1973 | Semler | 128/710 |
| 4,004,578 | 1/1977 | Palmius | 128/640 |
| 4,080,961 | 3/1978 | Eaton | 128/418 |
| 4,085,739 | 4/1978 | Sams | 128/410 |
| 4,120,305 | 10/1978 | Rhoads et al. | 128/783 |
| 4,122,843 | 10/1978 | Zdrojkowski | 128/644 |
| 4,166,457 | 10/1979 | Jacobsen et al. | 128/639 |
| 4,308,873 | 1/1982 | Maynard | 128/731 |
| 4,323,076 | 3/1982 | Sams | 128/644 |
| 4,599,483 | 7/1986 | Kuhn et al. | 174/36 |

FOREIGN PATENT DOCUMENTS

| | | | |
|---|---|---|---|
| 676273 | 7/1979 | U.S.S.R. | 128/644 |
| 204616 | 7/1983 | U.S.S.R. | |

Primary Examiner—William E. Kamm
Assistant Examiner—Randy Citrin
Attorney, Agent, or Firm—Daniel C. Abeles

[57] ABSTRACT

An electroencephalographic (EEG) cap for a human head for use in an evoked potential autorefractometry system which includes an adjustable headband having relatively rigid straps crossing over EEG measurement regions. Inserted through the straps are self-preparing electrodes which are connected to shielded cables. The self-preparing electrodes penetrate a dead skin layer without causing bleeding during positioning of the cap and do not require a previously prepared electrode positioning site. An electrolyte solution can be applied to the electrodes and the regions for measurement after the cap is in position by an electrolyte solution pump system. The entire cap can be shielded by a metal shield dome and held in place by a chin strap.

20 Claims, 10 Drawing Figures

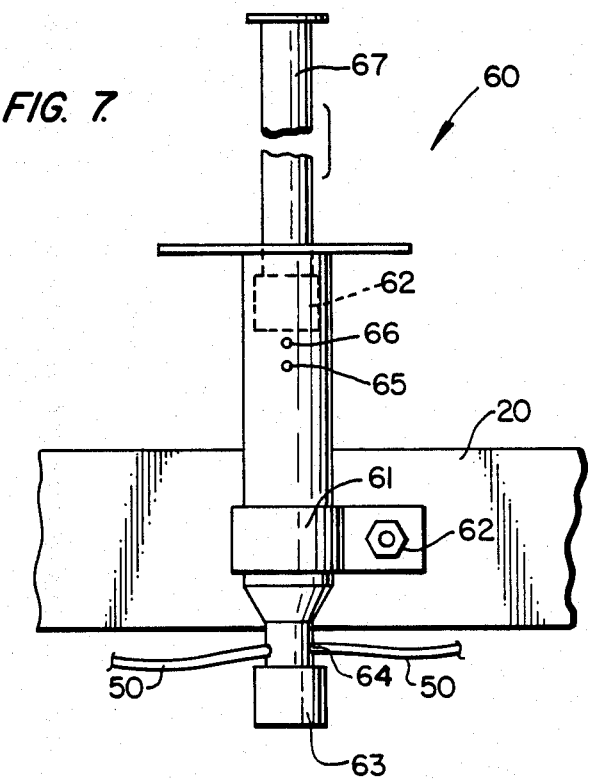
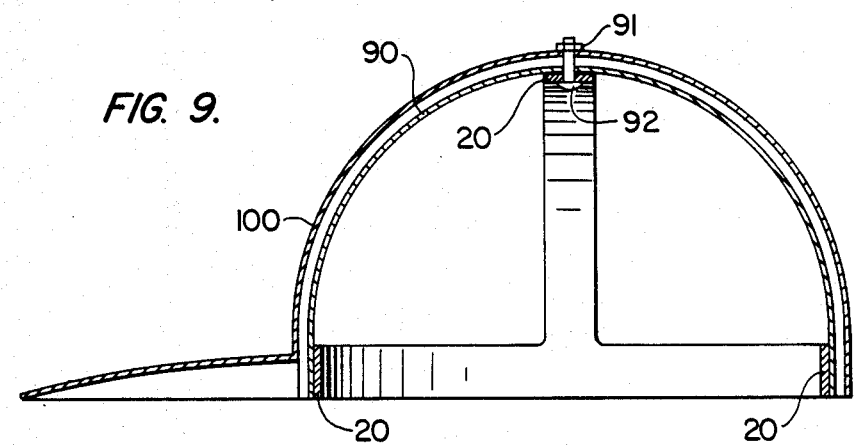

ELECTROENCEPHALOGRAPHIC CAP

CROSS-REFERENCES TO RELATED APPLICATIONS

This application is related to the following concurrently filed copending U.S. applications, all assigned to the assignee of the present invention: Low Noise Electroencephalographic (EEG) Probe Wiring System by Sherwin, having U.S. Ser. No. 727,060; Narrow Band EEG Amplifier by Sherwin and Zomp having U.S. Ser. No. 727,056; Subcaratinaceous EEG Probe by Sherwin and Mohan, having U.S. Ser. No. 727,033; Shielded Self-Preparing Electrode Suitable for EEG Mapping by Sherwin, having U.S. Ser. No. 727,058; and Evoked Potential Autorefractometry System, by Bernard, Roth, Mohan, Sherwin and Zomp, having U.S. Ser. No. 727,032.

BACKGROUND OF THE INVENTION

1. Field of the Invention

The present invention is directed to an electroencephalographic (EEG) cap for making EEG measurements and, more particularly, is directed to an EEG cap having self-preparing electrodes, for use in an evoked potential autorefractometry system which prescribes eyeglass lenses as described in the copending application mentioned above.

2. Description of the Related Art

FIG. 1A illustrates a prior art flexible EEG cap 10 having non-self-preparing electrodes 11 attached to flexible fabric 12 of the cap 10. The electrodes 11 do not directly contact the skin of the patient, but do so through an electrolyte cream. When this cap 10 is used, a blunt hypodermic needle must be inserted into a hole 13 in each electrode 11 and used to abrade the underlying skin to remove a keratinous layer or dead layer of skin so that the electrolyte cream, which is ejected from the syringe during removal will provide electrical contact between an epidermis layer of skin and the electrode 11.

If the hair beneath the point of contact of the electrodes 11 in the prior art cap 10 is very thick, it is sometimes necessary to cut the hair in order to allow the electrodes 11 to get close enough to the scalp so that the electrode cream does not create excessive resistance. FIG. 1B illustrates the details of the prior art cap electrode 11 in more detail. A plastic electrode body 14 is held to the fabric 12 by a press fit gromet 15, includes a metal conductor or slug 16 and forms a cavity 17 between the skin and the conductor 16. When electrolyte cream is injected through hole 13, it completes the electrical connection to the skin.

This prior art cap 10 is not suitable for commercial use in an evoked potential autorefractometry system because it is intimidating to potential patients and great discomfort is caused during the preparations for EEG measurement due to the necessary abrasion of the skin. The process undesirably requires the application of substantial amounts of electrode cream which patients remove from the hair by washing for cosmetic purposes after the cap 10 is removed. The electrical conductors 18 traveling from the electrodes 11 to the testing apparatus are not shielded and can pick up substantial amounts of environmental noise which makes the measurement of EEG signals much more difficult. In addition, different size caps 10 must be provided for patients of different sizes. The prior art cap 10 and electrodes 11 are described in more detail in U.S. Pat. Nos. 4,085,739 and 4,323,076.

SUMMARY OF THE INVENTION

It is an object of the present invention to provide an EEG cap suitable for commercial use that does not intimidate, cause discomfort or produce cosmetic problems for the patient.

Another object of the present invention is to provide an EEG cap which reduces the preparation time for the subject.

An additional object of the present invention is to provide an EEG cap which does not require that hair be cut beneath the electrodes.

A further object of the present invention is to provide a cap which does not leave substantial amounts of electrolyte in the hair.

An additional object of the present invention is to provide an EEG cap which is resistant to electrical noise from the environment.

Yet another object of the present invention is to provide an EEG cap in which the electrodes can be disguised or hidden.

The above objects can be accomplished by an EEG cap which includes an adjustable rigid headband for fixing self-preparing electrodes relative to scalp measurement regions where the electrodes are shielded and connected by a shielded cable to a measurement apparatus. The self-preparing electrodes require no prior preparation of the site on the skin where the electrode is positioned and penetrate a dead layer of skin without causing bleeding. Also included is an optional electrolyte pumping system for applying an electrolyte to the scalp after the cap is positioned. A retaining chin strap or dome electrical shield can be provided to help retain the cap on the head.

These, together with other objects and advantages which will be subsequently apparent, reside in the details of construction and operation of the cap as more fully hereinafter described and claimed, reference being had to the accompanying drawings forming a part hereof, wherein like numerals refer to like parts throughout.

BRIEF DESCRIPTION OF THE DRAWINGS

FIG. 7 illustrates a clamp that can be used to retain the wiring cables 40 and the electrolyte tube 50 of the cap in FIG. 2;

FIG. 9 illustrates the details of a metal shield dome 90 for electrically shielding the head and a baseball cap 100 for disguising the EEG cap.

DESCRIPTION OF THE PREFERRED EMBODIMENTS

Figure 1A:
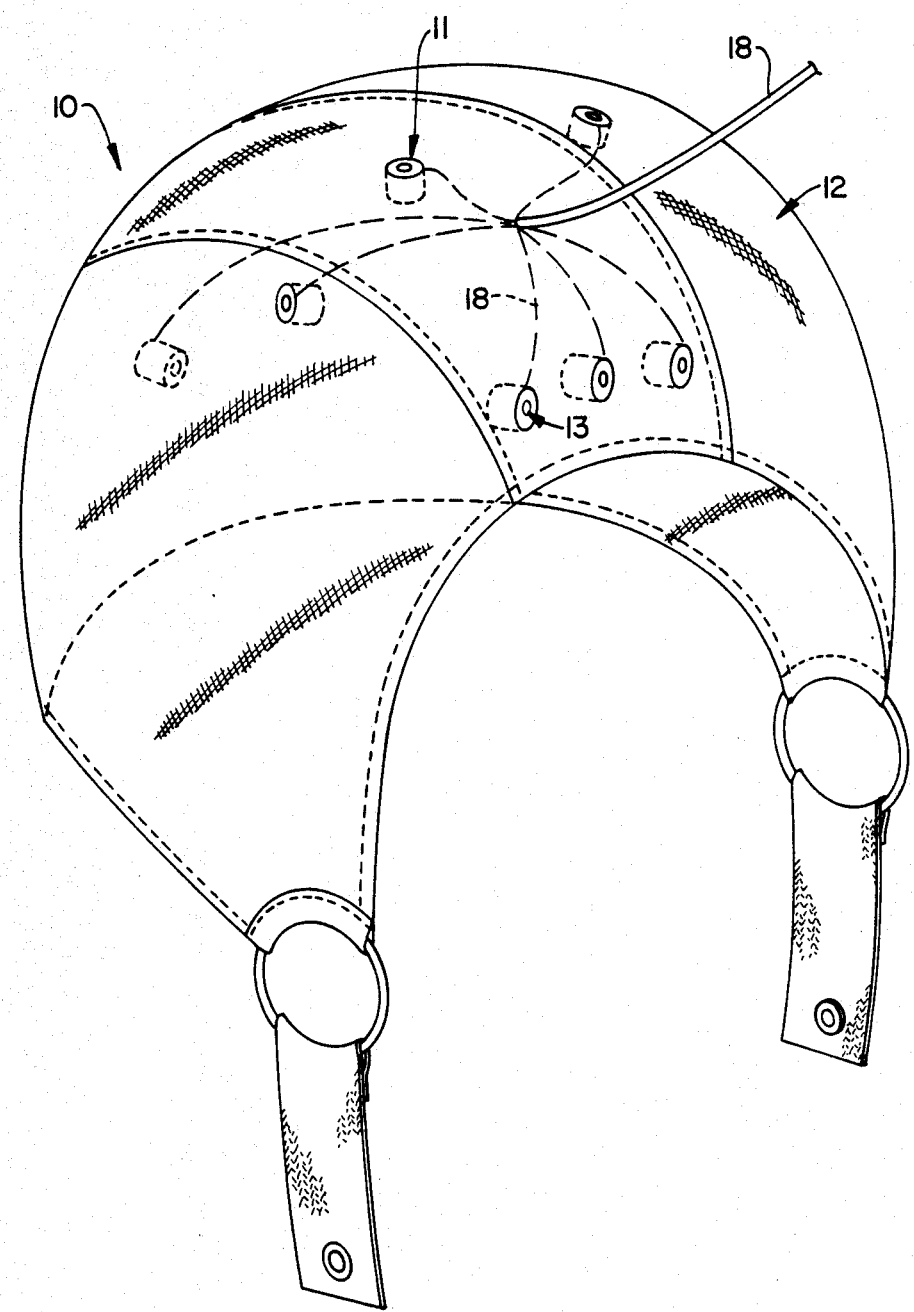
FIGS. 1A and 1B illustrate a prior art flexible fabric EEG cap 10 having non-self-preparing electrodes 11 and unshielded wiring 18.
Figure 2:
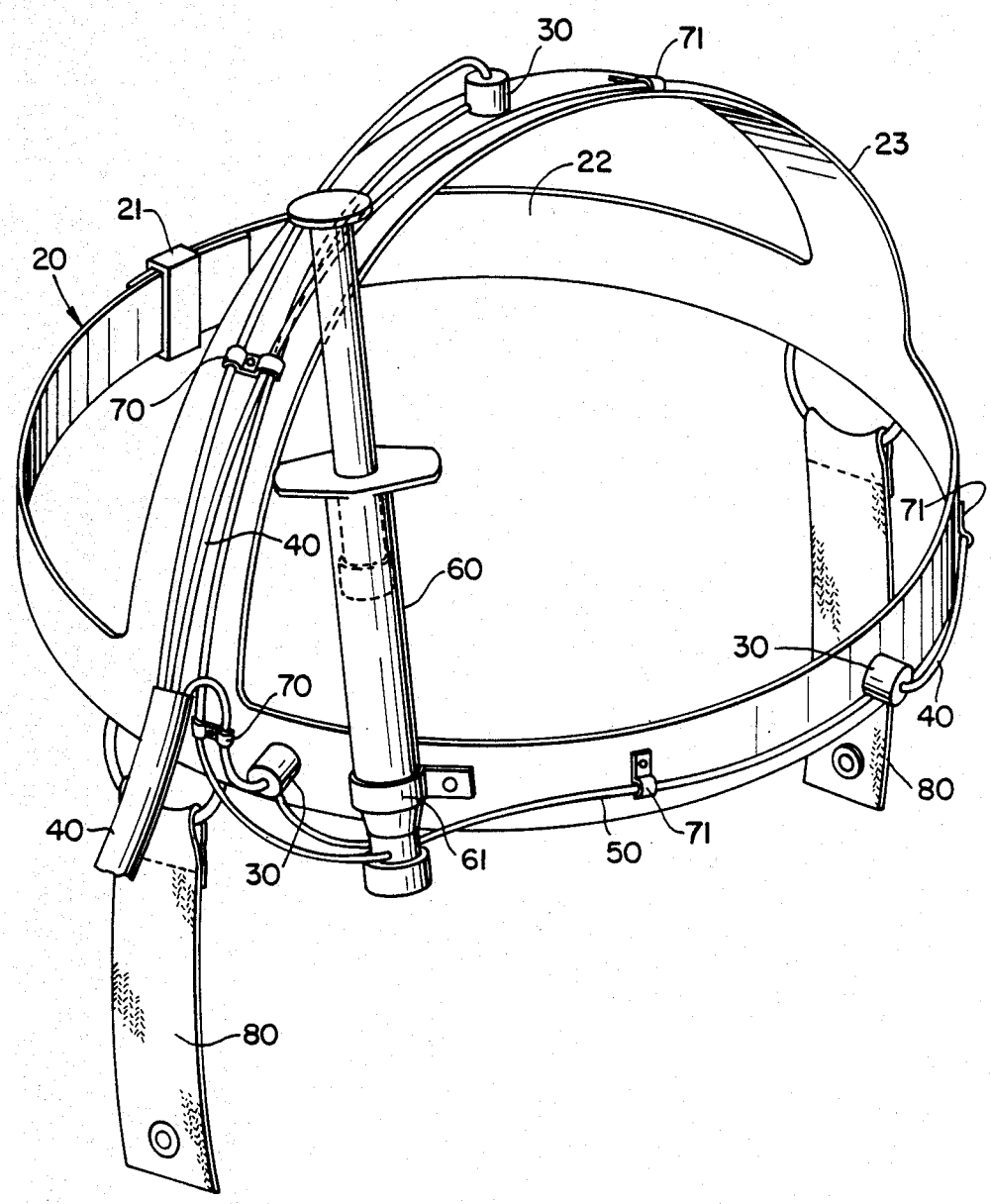
FIG. 2 is a perspective view of an EEG cap according to the present invention.
Figure 1B:
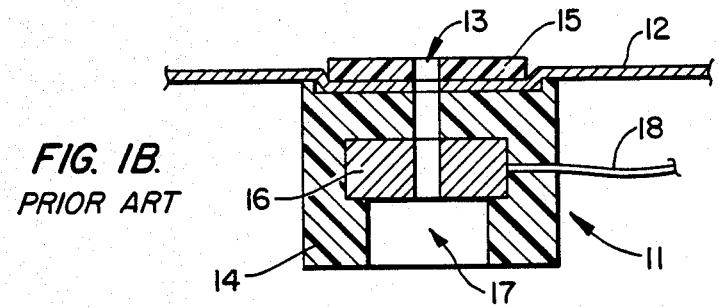

FIG. 2 illustrates an EEG cap according to the present invention which includes an adjustable headband 20 having a headband adjustor 21 on the front of the headband 20 for adjusting a horizontal band or a brow strap 22 which encirles the head and may be adjusted for proper head size. Also included is at least one diametric or radial top strap 23 crossing over the top of the head. Self-preparing electrodes 30 are mounted through the straps 22 and 23 at locations appropriate for the desired EEG measurements and electrode configuration. Connected to each of the electrodes 30 is a shielded cable 40 for conducting the EEG signals to the measurement apparatus. Situated adjacent to and in proximity with each electrode 30 is an electrolyte tube 50 for conveying an electrolyte solution from an electrolyte pump 60. The electrolyte fluid pumping system delivers a small amount of conductive fluid to the base of each electrode 30 after the cap has been positioned and preceding EEG measurement to minimize the effective scalp or source impedance and maximize the output signal produced by the electrodes 30. The pump 60 is retained against the headband by a pump clamp 61. The cables 40 and tubes 50 are retained against the plastic headband by double clamps 70 and single clamp 71. An optional chin strap 80 can be used to retain the cap on the head of the subject.

Figure 3:
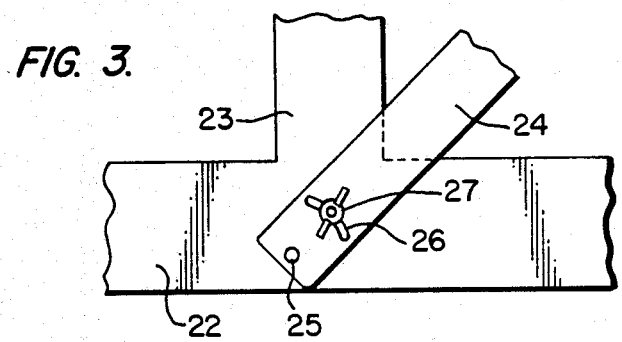
FIG. 3 depicts the details of an adjustable strap 25 that can be rigidly fixed over a scalp measurement region.

The headband 20 is preferably made of a rigid plastic such as found in conventional hard hats and chemical face shields and must be rigid enough to keep the electrodes 30 against the head by overcoming a spring action provided by the electrodes 30 wich are mounted in the brow strap portion of the headband 20. The strap 80 overcomes the spring force of the spring in the electrode 30 on top of the head. A suitable adjustable headband 20 can be obtained from U.S. Safety of Kansas City, Mo., type G3 or G4 headgear suspension. This headgear suspension is freely movable, allowing the patient to move his or her head, even to get up from the test chair. This headband inherently does not restrict patient movement. FIG. 2 illustrates a single radial or top strap 23; however, it is possible to provide as many straps 23 as is necessary to pass over the regions on the scalp of measurement interest. The electrode placement provided by the cap of FIG. 2 is particularly suitable for occipital lobe measurements useful in an evoked potential auto-refractometry system for diagnosing corrective lenses for the human eye as discussed in detail in the previously mentioned copending related application on that subject. If measurements are necessary from the frontal lobes, a frontal lobe strap for holding one or more electrodes 30 could be provided as long as the additional strap is rigidly connected to the adjustable brow strap 22 so that the electrodes 30 are firmly held in position. In such a situation, it would also be necessary to retain the top strap 23 for support. Caps with fixed relationship straps are very suitable for commercial application where the same measurements are repeatedly made for a number of subjects, such as in an optometrist's office. For experimental purposes, an adjustable headband 20, as illustrated in FIG. 2, could be fitted with an adjustable strap 24, as illustrated in FIG. 3.

The adjustable strap 24 pivots around a gromet or rivet 25 using slot 26 and wingnut/screw combination 27. When the appropriate position for the electrode is determined, the wing-nut and screw 27 can be tightened so that the adjustable strap is held rigidly with respect to the brow strap 22 and top strap 23.

Figure 4:
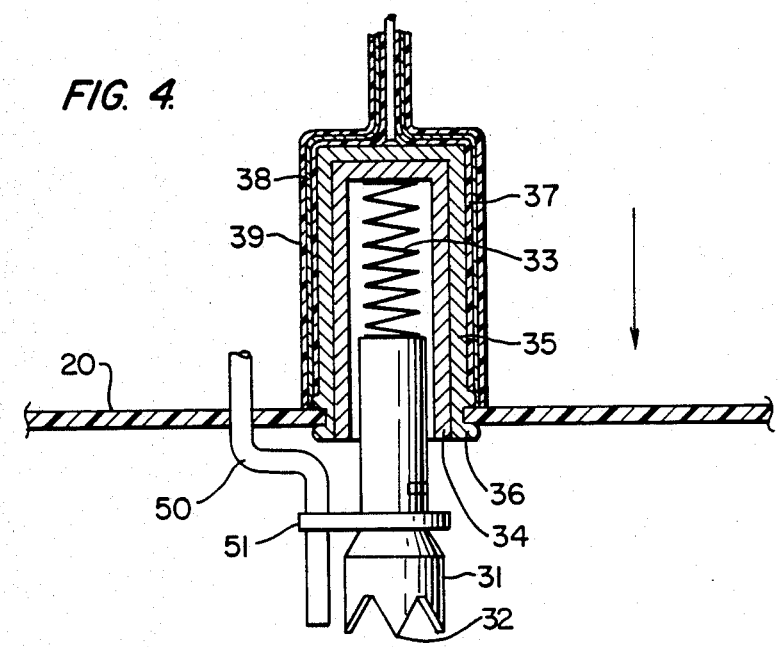
FIG. 4 illustrates the details of an electrode 30 and an electrolyte application tube 50 positioned adjacent thereto for the cap of FIG. 2.

FIG. 4 illustrates the details of the electrodes 30 which pass through headband 20. Each electrode 30 includes a tulip probe 31 extending inwardly of the head-band 20 and preferably having five very sharp tipped points 32. The probe 31 is urged toward the scalp by spring 33. The spring 33 and probe 31 are retained in a probe cartridge 34 which is removable and frictionally fits within probe cartridge holder 35 using a crimp roll. The tulip probe 31, probe cartridge 34 and spring 33 can be obtained from Ostby-Barton of Warwick, R.I. and are commonly used for electronic circuit testing. The tulip probe 31 is a self-cleaning probe which distributes force equally across the surface of the skin which it contacts. The spring 33 and arrangement of the sharp points 32 of the tip provide sufficient force (about 2.5 ounces) to penetrate the keratinous layer of skin without penetrating the epidermis layer and without causing bleeding. The spring 33 allows the probe 31 to move back into the cavity of the cartridge 34 inherently, mechanically stabilizing the tip of the probe 31. The probe cartridge holder 35 includes nipples 36 which form a structure similar to a crimp roll which will allow the cartridge to be snapped into the headband 20. The electrode cable 40 is soldered to the probe cartridge holder 35 using an electronic solder, the probe cartridge 35 is surrounded by a heat shrink tubing layer 37, a shield braid 38 and a second heat shrink tubing layer 39 which firmly locks the whole structure in place. The shield braid 38 runs all the way to the headband 20 and is connected to a shield of cable 40. Attached to the tulip probe 31 is a tube clamp 51 for retaining electrotube 50 adjacent to the probe tip points 32. The tube clamp 51 can be a simple wire clamp or a stamped piece of metal. The tube 50 can be used to deliver electrolyte from the pump 60 to the area of penetration of the probe 31 following application of the cap, but preceding testing to minimize the effective scalp impedance and maximize EEG signal output. If a silver coated tulip probe 31 is used, a silver salt electrolyte cream is preferred. Details concerning construction of alternate self-preparing electrodes can be found in the copending concurrently filed applications mentioned above in the cross references section directed to a shielded self-preparing electrode suitable for EEG mapping and a subcaratinaceous EEG probe.

Figure 5:
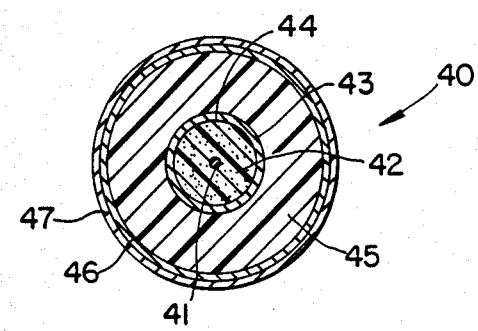
FIGS. 5 and 6 illustrate the construction of shielded cables 40 for the cap of FIG. 2.

FIG. 5 illustrates in cross-section the construction of a preferred shielded cable 40. Cable 40 includes a conductor 41 surrounded by polyethylene insulation 42 which is surrounded by a microdot cable shield 43. Inbetween the insulation 42 and shield 43 is a graphite layer 44. Around the microdot cable shield 43 is a Teflon insulating jacket 45 which is surrounded by a shield braid 46 which is connected to ground. The shield braid 46 is surrounded by shrink-wrap tubing 47 which acts as a further insulator. The conductor 41, insulation 42, shield 43, graphite layer 44 and Teflon jacket 45 can be obtained as a unit as a microdot cable from Microtech of Boothwyn, Pa. Suitable shield braid 46 and shrink wrap tubing can be obtained from an electronics supply house.

Figure 6:
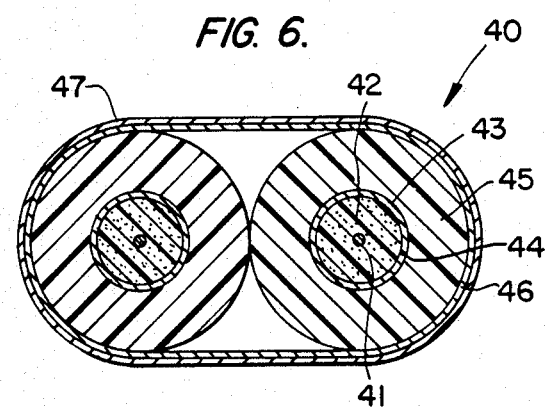

FIG. 6 illustrates the combination of three cables 40 into a cable bundle particularly showing that the shield braid 46 surrounds the entire cable bundle shielding it from electrical environmental noise. The shield braid 46 should be connected to ground. Additional details concerning the construction and characteristics of the shielded cable 40 are provided in the copending concurrently filed application directed to a low noise EEG wiring system mentioned in the cross references section. If a different wiring system is used, it should be an optimized electrically shielded cable so that noise will not be gathered by the wiring system; however, floating wires could be used if high quality amplifiers and filters are used.

In laying out the cable 40 path on the headband 20, care should be taken to minimize the length of the conductors or pigtails after they separate from the cable bundle. Minimizing pigtain length reduces the capture area for loop noise pick-up created by loops formed by the cables 40 and scalp through electrodes 30.

FIG. 7 illustrates the details of the pump 60 which is attached to the headband 20 by clamp 61 and nut/screw combination 62. Since the screw portion of the nut/screw combination 62 is on the inside of the headband, the screw surface should be rounded and/or flat to minimize discomfort to the patient. The pump 60 can be an off-the-shelf 5 cc syringe obtainable from a medical supply house as long as it includes a threaded syringe cap 63 which can be removed to empty the pump 60 or alternately used to fill the pump 60. The electrolyte solution is forced from the pump through tubes 50 by plunger 67 and plunger stopper 62. The tubes 50 enter the pump 60 though tube entry holes 64 which are formed using a cold needle, such as a darning needle. The cold darning needle is forced through the syringe and wallowed around to elastically expand the size of a tube hole 64. When the tube hole 64 is large enough to insert tube 50, the tube 50 is inserted and the plastic of the syringe elastically contracts back around the tube 50 to provide a pressure seal. Drilling or using a hot needle is not suitable for making holes 64 because elastic contraction of the holes will not occur if they are created by melting. The tubes should also not be glued to the syringe. Because of the closing or crimping action provided by the pump 60, after the tubes are inserted into holes 64, the tubing must be relatively rigid and resist collapse when squeezed with the fingers. Teflon surgical grade tubing of size 3 mm internal diameter obtainable from a medical supply house is preferred.

The tubes 50 are thus removable from the pump 60 so that a cleaning fluid, such as water, can be forced through the tubes 50 to clean same. For reinsertion of a tube 50 after cleaning, the original cold needle used for puncturing should be used to wallow out the hole 63 again so that the tube 50 can be inserted and pressure sealed. Whenever the pump 60 is oriented vertically, it would be impossible to fill the pump through the end having the threaded syringe cap 63. As an alternate method of filling the syringe when it is vertically oriented, a fill hole 65 and air release hole 66 which will accept a standard heavy gauge hypodermic needle are provided.

Figure 8:
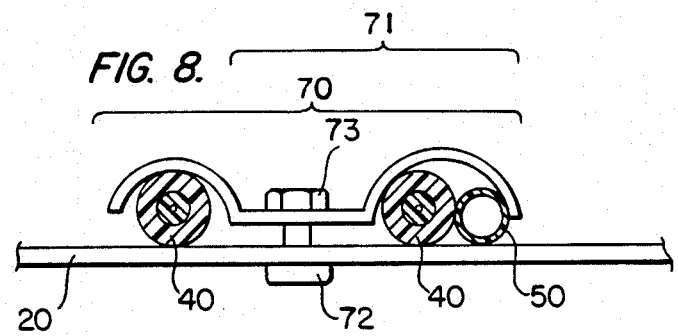
FIG. 8 illustrates the details of an electrolyte pump 60 and tubes 50 connected thereto for the cap of FIG. 2.

FIG. 8 illustrates the double 70 and single 71 clamps and used to attach the cables 40 to electrolyte tubes 50 to the headband 20. The dashed line indicates the point of division of a double clamp 70 for obtaining a single clamp 71. The clamp can be attached to the headband using a screw 72 and wingnut 73 or a rivet. The screw 72 should be flat or round headed so that it does not cause discomfort to the patient. The screw 72 and wingnut 73 combination facilitates removal of the cables 40 and tubes 50 for testing and cleaning, respectively.

FIG. 9 illustrates the attachment of an optional metal shield dome 90 to headband 20 using the nut 91 and screw 92 combination. Once again, the screw 92 should be a flat or rounded head screw. The shield dome provides electrical shielding for the approximate one-half foot noise signal reception area provided by an exposed head and should be connected to the shield braid 45 of cable 40 or the reference lead near the ear. The shield 90 can be covered by a cap, such as a baseball cap 100, to disguise the cap so that the patients will not be overly intimidated by the cap. As an alternative, a metal baseball cap could be used in place of the shield dome 90.

The shield dome 90 also provides sufficient weight to overcome the spring force (approximately 2.5 ounces) provided by the electrode on top of the head and keep the electrode 30 forced against the skin. If the shield dome 90 is not used, a chin strap 80 or other elastic means for overcoming the spring action of the on the top of the head should be provided. The arrow in FIG. 4 indicated the required force direction for gravity when the dome 90 is used or when the force of the strap 80 is used to overcome the spring force.

During use, after the cap is positioned, a resistivity check should be conducted. The self-preparing electrodes 30 will usually provide a resistance of less than 5 kilohms after positioning. If the resistance is not low enough, the cap should be jiggled to cause the tulip probe 31 to further penetrate the dead skin layer. If additional lowering of the resistance is desired, an electrolyte, such as a saline solution or commercial electrode cream, can be applied to the skin and electrode 30 using the pump 60; however, after applying the electrolyte, the pump should be operated briefly in a reverse direction to remove excess electrolyte and to break the electrical connection back to the pump through the electrolyte. If a shielded electrode such as described in this application or the previously mentioned copending applications is used in conjunction with a low noise EEG probe wiring system and a narrow band EEG amplifier, also mentioned in the copending applications section, a resistance substantially over 5 kilohms will be acceptable.

As described above, it is apparent that the present invention is particularly suitable for use in a commercial environment, such as an optician's office, where eyeglass prescriptions can be prescribed using the evoked potential autorefractometry system mentioned in the cross-reference section.

The many features and advantages of the invention are apparent from the detailed specification and, thus, it is intended by the appended claims to cover all such features and advantages of the cap which fall within the true spirit and scope of the invention. Further, since numerous modifications and changes will readily occur to those skilled in the art, it is not desired to limit the invention to exact construction and operation as described, and, accordingly, all suitable modifications and equivalents may be resorted to falling within the scope of the invention. For example, a special pump could be manufactured that includes a closed end and fill holes or a motor-driven pump could be located remotely. An ear clip could be substituted for the electrode closest to the ear. The wiring could be molded into the headband or passed through hollows in the headband similar to stereo headbands. Other means could be provided for applying the electrolyte, such as a rupturable plastic sack in proximity to the tulip probe or the probe could have a hollow center.

We claim as our invention:

1. An electroencephalographic (EEG) electrode mounting cap for a patient's head having keratinous and epidermis layers of skin, comprising:
   an adjustable freely movable headband adapted to be carried and supported by the head and adapted to tightly fit the head when adjusted; and
   electrode means, attached to said headband at regions for measurement on the head, for electrically contacting the head in the regions for measurement and conducting EEG signals, said electrode means including stabilization means, adapted to be positioned substantially adjacent to the head, for mechanically stabilizing said electrode means, thereby mechanically stabilizing the electrical contact between the head and said electrode means.

2. a cap as recited in claim 1, wherein said means for contacting comprises a self-preparing electrode.

3. A cap as recited in claim 2, wherein said self-preparing electrode comprises:
   a signal localizing probe having sharp points; and
   a spring for urging the sharp points through the keratinous layer of skin.

4. A cap as recited in claim 3, wherein said self-preparing electrode is electrically shielded.

5. A cap as recited in claim 1, wherein said means for contacting includes means for penetrating a keratinous layer of skin without causing bleeding and providing a penetrating force of approximately 2.5 ounces.

6. A cap as recited in claim 1, further comprising a shielded cable operatively connected to said means for contacting.

7. A cap as recited in claim 6, wherein said shielded cable comprises:
   a center conductor;
   a first insulation layer around said center conductor;
   a graphite layer around said first insulation layer;
   a cable shield around said graphite layer;
   a second insulation layer around said cable shield;
   a shield braid around said second insulation layer; and
   a third insulation layer around said shield braid.

8. A cap as recited in claim 1, further comprising electrolyte solution application means, attached to said headband, for applying an electrolytic solution to the regions of measurement and said means for contacting.

9. A cap as recited in claim 8, wherein said electrolyte solution application means comprises:
   a pump, attached to said headband, for pumping the electrolyte solution; and
   tubes, coupled to said pump, positioned adjacent to said means for contacting and attached to said headband, for applying the electrolyte solution to the regions of measurement and said means for contacting after contact has been made.

10. A cap as recited in claim 1, further comprising means for electrically shielding said means for contacting.

11. A cap as recited in claim 1, further comprising electrical shield means for electrically shielding both the head and said electrode means.

12. A cap as recited in claim 1, further comprising retaining means, coupled to said adjustable headband, for retaining the cap upon the head during head movement.

13. A cap as recited in claim 12, wherein said retaining means comprises an adjustable chin strap.

14. A cap as recited in claim 12,
    wherein said means for contacting comprises:
    a probe having sharp points; and
    a spring for urging the sharp points through the keratinous layer of skin with a spring force; and
    wherein said cap further comprises electrical shield dome means, coupled to said adjustable headband, for electrically shielding said probe and the head, and having a weight sufficient to overcome the spring force of said spring so that said probe penetrates the keratinous layer of the skin.

15. A cap as recited in claim 1, wherein said adjustable headband is formed from rigid plastic and comprises:
    an adjustable browband adapted for tightly circling the head horizontally;
    a top band adapted for tightly running across the top of the head and rigidly attached to said adjustable browband; and
    at least one band adapted for crossing the regions of measurement and attached to said adjustable browband.

16. A cap as recited in claim 15, wherein said at least one band is rigidly attached to said adjustable browband.

17. A cap as recited in claim 15, wherein said at least one band is movably attached and rigidly fixable to said adjustable browband.

18. A cap as recited in claim 17, further comprising conductive dome shield means, attached to said adjustable headband, for electrically shielding said self-preparing electrodes, said shielded cable and the head.

19. A cap as recited in claim 17, further comprising a chin strap attached to said adjustable headband.

20. An electroencephalographic (EEG) electrode mounting cap for a human head for use in an evoked potential autorefractometry system, said cap comprising:
    an adjustable freely movable headband adapted to be carried and supported by the head, adapted to tightly fit the head when adjusted, having straps rigidly fixed with respect to each other and the straps adapted to pass over measurement regions of the head where EEG measurements are to be made;
    self-preparing electrodes attached to the straps in positions to electrically contact the measurement regions using an electrode tip and without requiring scalp preparation, and including mechanical stabilization means for mechanically stabilizing the contact between the tip and the corresponding measurement region;
    an electrically shielded cable operatively connected to said self-preparing electrodes;
    a piston type electrolyte solution pump, having a manifold, attached to said adjustable headband, and adapted for pumping an electrolyte solution; and
    tubes attached to said adjustable headband, coupled to the electrolyte solution pump, positioned adjacent to the electrode tips, and adapted for applying the electrolyte solution to the measurement region and the electrode tip.

* * * * *